United States Patent
Fanelli et al.

(10) Patent No.: US 6,808,519 B2
(45) Date of Patent: Oct. 26, 2004

(54) PERCUTANEOUS GASTROSTOMY DEVICE AND METHOD

(75) Inventors: Robert D. Fanelli, Dalton, MA (US); Tamisha H. Clark, Pfafftown, NC (US)

(73) Assignee: Wilson-Cook Medical Incorporated, Winston-Salem, NC (US)

( * ) Notice: Subject to any disclaimer, the term of this patent is extended or adjusted under 35 U.S.C. 154(b) by 0 days.

(21) Appl. No.: 09/852,811

(22) Filed: May 10, 2001

(65) Prior Publication Data

US 2002/0002361 A1 Jan. 3, 2002

Related U.S. Application Data

(60) Provisional application No. 60/205,185, filed on May 18, 2000.

(51) Int. Cl.[7] ........................ A61M 25/00; A61M 31/00; A61B 1/04; A61F 11/00
(52) U.S. Cl. ........................ 604/523; 604/270; 604/910; 600/120; 606/108
(58) Field of Search ................................ 604/516, 104, 604/270, 523, 910, 174, 264; 600/127, 132, 129, 153, 120; 606/198, 108

(56) References Cited

U.S. PATENT DOCUMENTS

| | | | |
|---|---|---|---|
| 4,573,576 A | | 3/1986 | Krol |
| 4,668,225 A | * | 5/1987 | Russo et al. ................. 604/270 |
| 4,762,519 A | * | 8/1988 | Frimberger ............ 604/164.01 |
| 4,826,481 A | | 5/1989 | Sacks et al. |
| 4,836,481 A | | 6/1989 | Ceccarelli |
| 5,037,387 A | | 8/1991 | Quinn et al. |
| 5,084,014 A | | 1/1992 | Picha et al. |
| 5,112,310 A | | 5/1992 | Grobe |
| 5,152,756 A | | 10/1992 | Quinn et al. |
| 5,167,627 A | | 12/1992 | Clegg et al. |
| 5,259,367 A | | 11/1993 | Kirby et al. |
| 5,555,898 A | | 9/1996 | Suzuki et al. |
| 5,665,064 A | * | 9/1997 | Bodicky et al. ............ 604/516 |
| 5,728,178 A | | 3/1998 | Buffington et al. |
| 5,755,777 A | * | 5/1998 | Chuter ........................ 606/195 |
| 5,807,314 A | * | 9/1998 | Ross et al. ................... 604/500 |
| 5,851,196 A | | 12/1998 | Arnett |

* cited by examiner

Primary Examiner—Brian L. Casler
Assistant Examiner—Matthew DeSanto
(74) Attorney, Agent, or Firm—Brinks Hofer Gilson & Lione

(57) ABSTRACT

An apparatus and method for coupling a gastroscope (30) to a gastrostomy feeding tube apparatus (10) such that both can be introduced together into the alimentary tract, thereby eliminating the need to separately introduce the gastroscope afterward in order to verify that the gastrostomy feeding tube (11) has been correctly placed within the stomach of the patient. The gastrostomy feeding tube includes a coupling member (12), such as an elongate tract or thread, that is accessible about the second end (26) thereof. The elongate tract is drawn through the working channel (31) of the gastroscope by an engagement member (29), such as snare, which then allows the distal end (33) of the gastroscope to be advanced into the end cap (18) of the feeding tube so that the two can be pulled together into the stomach. In another embodiment, the coupling member comprises an integrated attachment member (39), such as hook, to which the engaging member can attach.

13 Claims, 3 Drawing Sheets

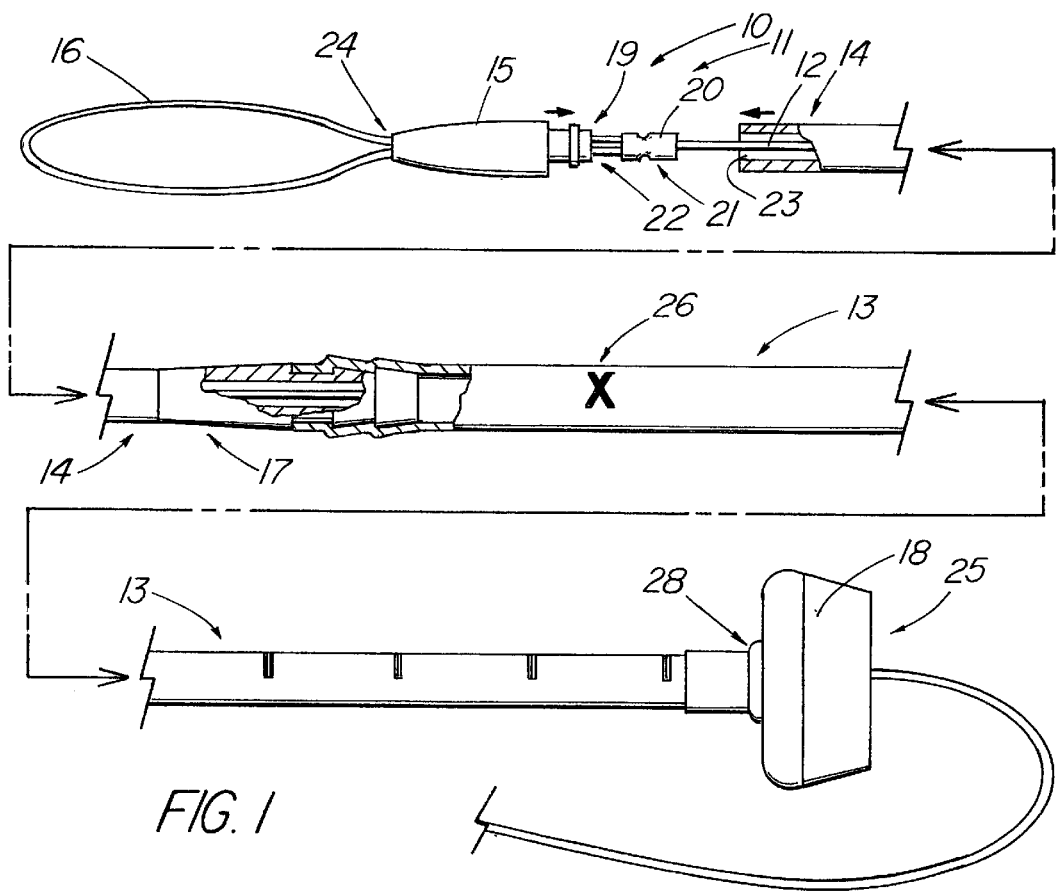
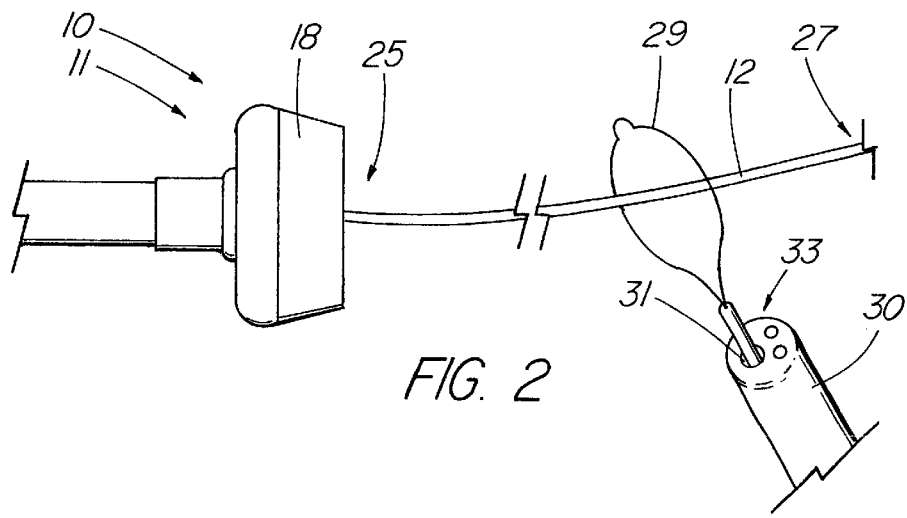
FIG. 1
FIG. 2

PERCUTANEOUS GASTROSTOMY DEVICE AND METHOD

CROSS-REFERENCE TO RELATED APPLICATIONS

This application claims priority of provisional application Ser. No. 60/205,185, filed May 18, 2000.

TECHNICAL FIELD

This invention relates to medical devices, more particularly to feeding tubes for delivery of nutritional products to the intestinal tract.

BACKGROUND OF THE INVENTION

Patients for which normal ingestion of food becomes difficult or impossible, may require placement of a feeding tube to assist in providing their nutritional needs. For some individuals, such as comatose patients, stroke victims, or those with a compromised gastrointestinal tract, this may require placement of a tube that is introduced percutaneously into the stomach for delivery of nutritional products directly into the stomach or jejunum. The procedure, known as a Percutaneous Endoscopic Gastrostomy (PEG), involves introduction of a gastroscope into the stomach, while the desired site where the stoma is to be created is indicated from above by depressing the abdomen. A sheathed needle punctures the abdominal wall and enters the stomach, creating a stoma. The needle is removed and a looped insertion wire is introduced through the sheath where it is grasped by a snare deployed from the working channel of the gastroscope. Once it is captured, the insertion wire is pulled into the channel of the gastroscope. The gastroscope is then withdrawn from the patient via the oral cavity, pulling the wire with it. In the standard Ponsky method (or "pull" method), the distal loop of a percutaneous gastrostomy feeding tube is coupled to the insertion wire loop exiting the patient's mouth. With the insertion wire now tethered to the gastrostomy feeding tube, the endoscopist then retracts the insertion wire exiting the stoma, thereby pulling the gastrostomy feeding tube into the patient's mouth and on toward the stomach. The tapered dilator portion aids in allowing the gastrostomy feeding tube to pass through the stoma. Once the tube has been properly positioned with the end cap snug against the internal wall of the stomach, the dilator portion of the gastrostomy feeding tube is cut away. Finally, the internal position of the gastrostomy feeding tube is checked by reintroducing the gastroscope.

In the variation of the PEG procedure known as the "push" method, the gastrostomy feeding tube is not tethered to the suture and pulled back through the gastrointestinal tract, but rather it is advanced or pushed down the esophagus by the physician and into positioned in the stomach, using a wire that has been placed in the same manner as the suture in the "pull" method. As with the "pull" method, the gastroscope is usually reintroduced to verify that the end cap is properly positioned against the stomach wall.

A disadvantage of most of the standard methods used to place a gastrostomy feeding tube is the need to reintroduce the gastroscope after placement to ensure that the end cap is in the correct position. This causes discomfort to the patient, yet eliminating this safeguard can result in the gastrostomy feeding tube not being properly positioned against the stomach wall. What is needed is a gastrostomy feeding tube and method for placement where the step of separately introducing the gastroscope is eliminated, while still having the benefit of using it for verification of gastrostomy feeding tube placement.

SUMMARY OF THE INVENTION

The foregoing problems are solved and a technical advance is achieved with illustrative gastrostomy (or PEG) feeding tube apparatus comprising a gastrostomy feeding tube and a coupling member, such as an elongate tract for allowing an endoscope, such as a gastroscope, to be coupled to, and introduced along with, the gastrostomy feeding tube. In one aspect of the invention, the elongate tract comprises an elongate thread member made of a polymer (synthetic) material, natural fiber, metal wire, etc., that is attached near the loop end of the gastrostomy feeding tube where it extends through the passageway and exits the second (end cap) end. The elongate tract is sufficiently long and sized in diameter such that it can be drawn through the working channel of a gastroscope using an engaging member, such as a standard polypectomy-type snare, which is then withdrawn out the proximal end of the gastroscope. This allows the gastroscope and gastrostomy feeding tube to be coupled together after the insertion wire has been drawn through the alimentary tract and exits the patient's mouth, allowing for safe and atraumatic introduction of the scope along with gastrostomy feeding tube as the latter is being placed within the patient. Otherwise, the gastroscope requires a separate introduction to confirm correct placement of the gastrostomy feeding tube, thus adding trauma and possible risk to the patient.

In another aspect of the invention, the coupling member comprises an attachment point, such as a hook, loop, or other structural element or apparatus for facilitating engagement with the engaging member of the gastroscope or an ancillary device or instrument to allow the gastroscope to be coupled with the gastrostomy feeding tube such that the gastroscope can be pulled down the throat and into the stomach along with the gastrostomy feeding tube. To engage the attachment point on the coupling member, the gastroscope itself can be modified to include an engagement mechanism, such as a loop, hook, etc., or the engaging member can comprise a separate snare, hooked stylet, etc. that can be introduced through the working channel of the scope to engage the attachment point, thereby allowing the distal end of the gastroscope to be drawn inside of the end cap and coupled thereto for introduction into the patient.

BRIEF DESCRIPTION OF THE DRAWINGS

FIG. 1 depicts a partially sectioned side view of an embodiment of the present invention;

FIGS. 2–6 depict a series of steps for placement of the present invention with the assistance of an gastroscope.

DETAILED DESCRIPTION

Figure 3:
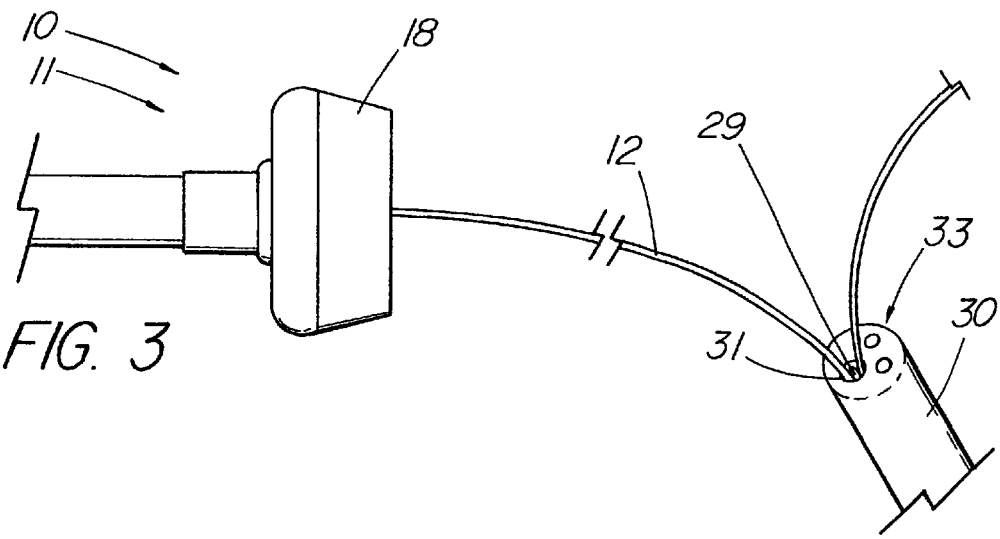

FIG. 1 depicts a partially sectioned side view of an embodiment of the present invention that includes a gastrostomy feeding tube apparatus 10, comprising a gastrostomy feeding tube 11, such as a pull-type percutaneous endoscopic gastrostomy (PEG) feeding tube, having a first end 24 and a second end 25 and further including a coupling member 12, such as an elongate tract 12, which is adapted for allowing an endoscope to couple with the apparatus. The elongate tract 12 comprises an elongated thread or suture made of a braided or monofilament polymeric material, a natural fiber, metal wire, or other suitable material. The elongate tract can be permanently or releasably attached to the gastrostomy feeding tube 11 and preferably extends for 130 cm or more beyond the second end 25 of the gastrostomy feeding tube 11, or of a distance that is able to accommodate the entire length of an endoscope working (internal) channel, such as a gastroscope. This distance varies according to the model of endoscope being used. The elongate tract 12 is captured by an engaging member 29, which could include a snare, forceps, or some other retrieval type device or mechanism, which typically resides within the working channel 31 of the endoscope 30 (FIG. 2). As will be described later in more detail, the gastroscope 30 advances over the elongate tract 12 that traverses the gastroscope's working channel 31 as the tube 11 and gastroscope are pulled together from the oral cavity into the stomach. In the illustrative embodiment of FIG. 1, the gastrostomy feeding tube 11 represents a modification of the PEG 24™ Percutaneous Endoscopic Gastrostomy System (Wilson-Cook Medical Inc., Winston-Salem, N.C.) which includes a discardable first portion 14 having a dilator tip 15 at the first end of the gastrostomy feeding tube 11, and a second, feeding tube portion 13 that is coupled to the distal portion 14 with a connector 17. An end cap 18 or 'tulip tip' is located at the second end 25 of the device. A distal coupling element 16, typically a wire loop, used in placement of the device to couple to an insertion wire (not shown), is located at the first end 24 of the gastrostomy feeding tube 11 where it extends from passageway 22 of the dilator tip 15. The two ends 19 of the loop 16 are fastened together inside the passageway 22 with an attachment means 20, such as a crimped metal cannula.

The dilator portion 14, including the dilator tip 15, are used to facilitate passage of the device out through the stomach wall and abdominal incision as the device is placed. Placement occurs when the end cap 18, the portion that remains within the stomach, abuts the stomach wall. Following placement of the gastrostomy feeding tube apparatus 10, the gastrostomy feeding tube 11 is secured at the entry site, usually with a bolster, then the dilator portion 14 is cut away at a designated cut point 26, leaving only the feeding tube portion 13 extending outward from the opening in the stomach of the patient.

The improvement of the gastrostomy feeding tube apparatus 10 lies in the addition of the coupling member 12, such as the illustrative elongate tract 12. In the illustrative embodiment, the elongate tract 12 is a braided polymeric thread or suture; however, a natural fiber thread, a single or multifilament wire or any elongated strand or strands of suitably strong material can be used. Generally, the elongate tract 12 should have good tensile strength and preferably, but not essentially, be resistant to cutting to prevent accidental severing of the elongate tract 12 when the dilator portion 14 of the apparatus is cut away from the feeding tube portion 13. It is not critical that the elongate tract 12 remain intact at that time; however, since the severed portion of the elongate tract 12 (including the free end 27) can be removed through the gastroscope 30 through which it has already been fed. One elongate tract 12 material with desirable properties is VECTRAN® fiber (Celanese Chemicals, Dallas, Tex.). The preferred diameter of the illustrative elongate tract 12 made of VECTRAN® is 0.040" to 0.100", however, the upper diameter is truly limited only by the minimum passageway diameter of the feeding tube. The minimum diameter of the elongate tract 12, at which inadvertent breakage would not readily occur, depends primarily on the material used, and generally there is not a need to approach the minimum safe diameter, given the relatively large size of the feeding tube passageway and endoscope working channel.

While the elongate tract 12 conceivably could be attached almost anywhere about the passageway 23 of the gastrostomy feeding tube 11, it is generally preferred that the attachment point be on the first portion 14 side of the designated cut point 26 such that when the first portion 14, including the connector 17, are cut away, the elongate tract 12 is removed with the discarded portion If the elongate tract 12 were to be attached about the end cap 18, for example, it could not be as easily removed from the patient by drawing it back through the working channel of the gastroscope. As previously suggested, if the elongate tract 12 is accidentally or intentionally severed with the dilator portion 14 of the apparatus 10, the two halves can still be removed separately generally provided that the elongate tract 12 is attached about the dilator portion 14 of the apparatus 10. In the illustrative embodiment, the elongate tract 12 is coupled to the distal loop 16 by the attachment means 20. The elongate tract 12 extends from the distal loop 16 through the passageway 23 of the gastrostomy feeding tube 11, exiting at the second end 25 thereof.

Figure 7:
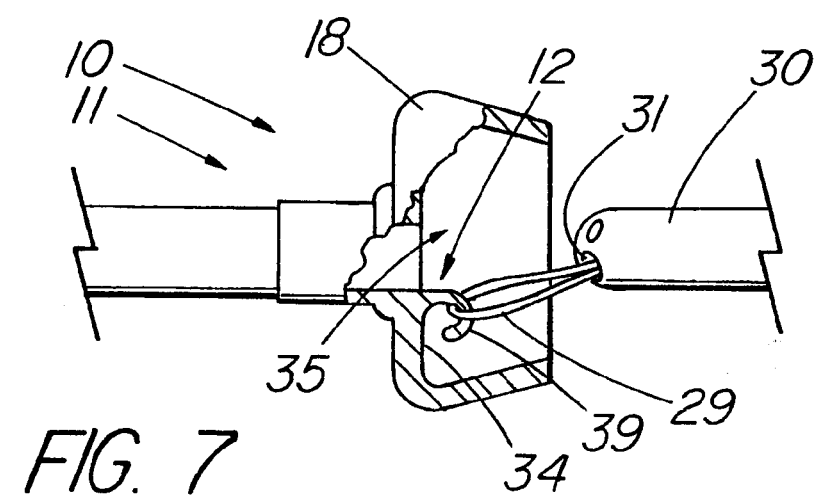
FIG. 7 depicts a partially sectioned side view of a second embodiment of the present invention.

In a second embodiment of the present invention shown in FIG. 7 (with further reference to FIG. 2), the coupling member 12 comprises an integrated attachment region 39, such as the illustrative hooked member, located about the second end 25 of the gastrostomy feeding tube 11. The hooked member 39 is adapted to be engaged by an engaging member 29, typically an ancillary device, such as a snare, that has been introduced through the working channel 31 of the gastroscope 30, or an engaging member 29, such as a loop or hook, that is integral with the distal end 33 of the gastroscope 30, itself. In the illustrative embodiment, the hooked member 39 extends outward from the inner surface 34 of the inner bowl 35 of the end cap 18, positioned such that it does not cause partial obstruction of the passageway 23 of the gastrostomy feeding tube 11. Rather than being drawn through the length of the working channel 31, like the elongate tract 12, the hooked member 39 is engaged by a snare 29, such that the distal end 33 of the gastroscope 30 can be drawn into the end cap 18 of the gastrostomy feeding tube 11 so that the tube and scope can be introduced together into the stomach of the patient. The snare 29 is then left within the gastroscope until the assembly 10 reaches the placement site. The gastroscope 30 is then disengaged from the gastrostomy feeding tube 11 by extending the snare 29 and slipping it off the hooked member 39. Correct placement of the end cap 18 against the stomach wall is then verified. The integrated attachment region 39 can comprise any suitable structure(s) to which a corresponding engaging member 29 can attach or become coupled with, including a fixed or retractable loop, hook, snare, screw or locking mechanism, etc. The integrated attachment region 39 can comprises a protuberance extending from the apparatus 10, as shown, or it can comprises a recessed area into which the engaging member 29 is advanced.

Figure 4:
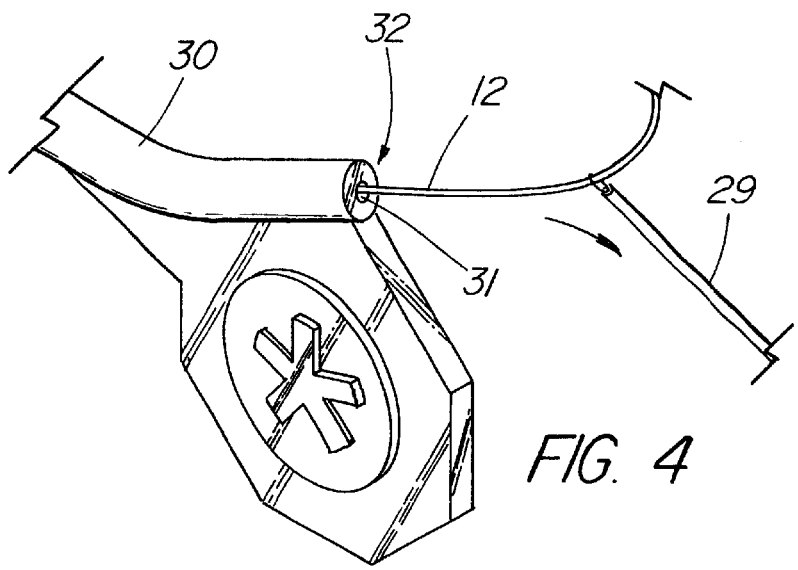
Figure 5:
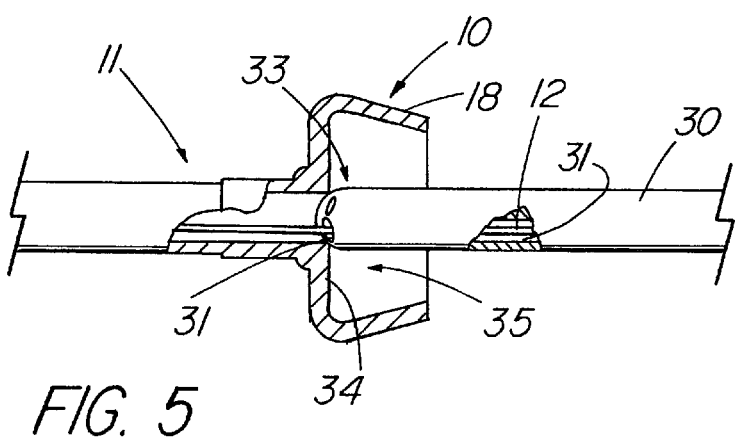
Figure 6:
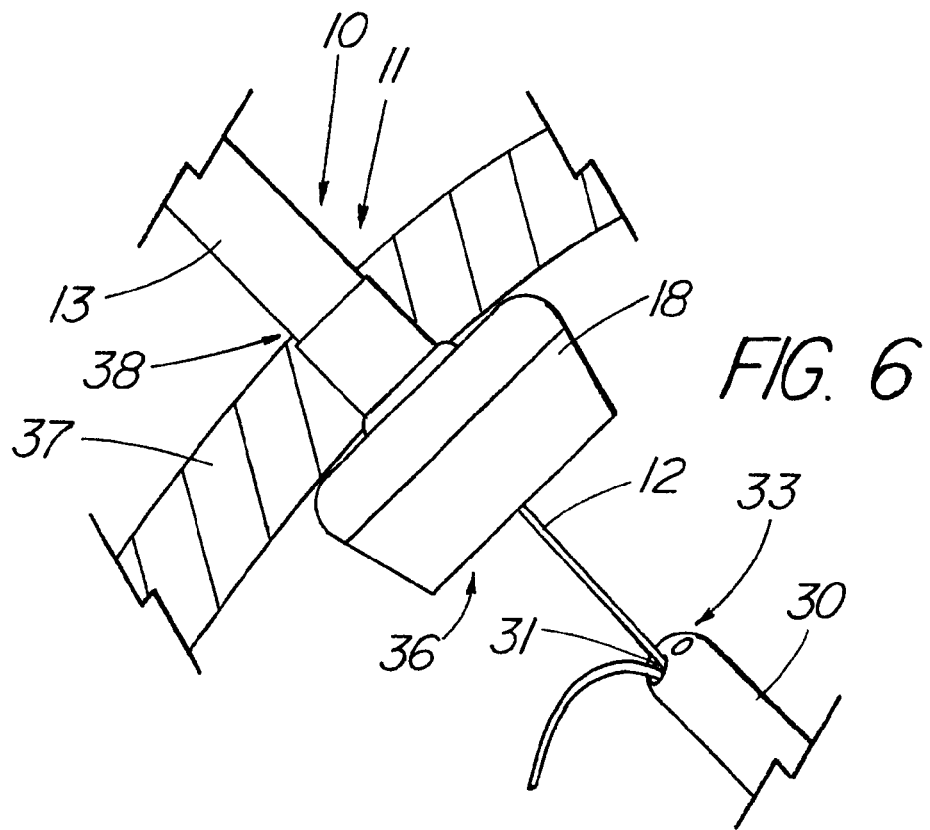

FIGS. 2–6 depicts how the elongate tract 12 of the embodiment of FIG. 1 functions to permit the gastroscope 30 to be reintroduced along with the gastrostomy feeding tube 11 to verify correct placement of the latter. The initial part of the gastrostomy feeding tube placement procedure, which is not illustrated, is the well-known pull or Ponsksy method of placing a standard PEG tube in which an insertion wire is introduced percutaneously through the stoma created by a needle cannula through stomach wall under endoscope visualization. The insertion wire is captured by a snare or hooked stylet extending from the gastroscope 30, at which time it is pulled out through the mouth of the patient along with the gastroscope 30. After the insertion wire has been drawn out of the mouth of the patient, it is coupled with the distal loop 16 of the gastrostomy feeding tube 11. An engaging member 29 such as a polypectomy-type snare 29 as depicted in FIG. 2, is advanced through the working channel 31 of the gastroscope 30. If appropriate, the same device may be used which was used to capture the insertion wire. Using the snare 29, the elongate tract 12 is then grasped about 2 cm from its free end 27. Other instrumentation would include forceps, hooked wires, baskets, or any well-known type of retrieval device compatible for use with an endoscope. An optional marking can be placed on the elongate tract 12 at the suggested point where it should be ensnared. The snare 29 is then withdrawn back into the working channel 31 of the gastroscope 30, thus drawing in the elongate tract 12, as shown in FIG. 3. The snare 29 is completely withdrawn through the working channel 31 of the gastroscope 30 until it exits the proximal end 32 thereof, as shown in FIG. 4. The snare 29 continues to grasp the elongate tract 12 as the gastrostomy feeding tube 11, which has been coupled to the insertion wire or suture, is pulled into the mouth. As that point, the gastroscope 30 is advanced over the elongate tract 12 until it abuts the inner surface 34 of the end cap 18 as depicted in FIG. 5. The inner bowl 35 of the end cap 18 acts to shroud the leading edge 33 of the gastroscope 30 which is generally maintained in contact with the inner surface 34 of the end cap 18 as the endoscope 30 and gastrostomy feeding tube 11 are drawn together into the alimentary tract of the patient. Thus, the gastrostomy feeding tube 11, with its dilator tip 15, provides a relatively safe and atraumatic introduction for the blunt-tipped gastroscope 30 which otherwise, would be separately introduced to verify placement of the gastrostomy feeding tube 11, resulting in possible trauma and additional discomfort to the patient. As the end cap 18 approaches its final position against the inner wall 37 of the stomach 36, the endoscopist released the tension on the elongate tract 12 and allows the gastroscope 30 to back away several centimeters from the gastrostomy tube, as depicted in FIG. 6, to allow the gastroscope 30 to view the placement site and verify that the end cap 18 properly abuts the inner wall 37. At that point, a bolster (not shown) is typically placed over the gastrostomy feeding tube 11, external to the stoma, and the tube is severed at the cut point 26 (shown in FIG. 1). If the elongate tract 12 is left intact after cutting the gastrostomy feeding tube 11, as recommended, then it can be removed with the discarded dilator portion 14 of the apparatus 10. If it is accidentally cut, then the severed portion inside the patient can be removed through the working channel 31 of the gastroscope 30 by applying traction to pull it through.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention.

What is claimed is:

1. A percutaneous gastrostomy feeding tube apparatus adapted for placement in a patient using an endoscope, said apparatus comprising:
    a gastrostomy feeding tube having a passageway extending therethrough, a distal end, a proximal end, a removable first portion and a second portion, the removable first portion, which includes the distal end, being adapted to be removed from the second portion and being configured and adapted for introducing the second portion within the stomach of a patient, the second portion including a passageway extending therethough and an end cap located about the second end, the end cap having an inner surface; and
    an elongate tract adapted for passage through a channel of the endoscope, the elongate tract having a distal end and a proximal end, the distal end of the elongate tract adapted to be attached about the first portion of the gastrostomy feeding tube, the tract extending through the passageway and beyond the end cap, wherein the distance of the tract from the inner surface of the end cap to the proximal end of the tract is configured to exceed the length of the endoscope channel.

2. The apparatus of claim 1, wherein the elongate tract extends at least 130 cm from the distal end of the gastrostomy feed tube.

3. The apparatus of claim 1 wherein the elongate tract comprises a braided polymer.

4. A percutaneous gastrostomy feeding tube apparatus adapted for placement in a patient using an endoscope, said apparatus comprising:
    a gastrostomy feeding tube having a passageway, a distal end, a proximal end adapted to receive and engage the endoscope, and an end cap located about the proximal end, the distal end including a discardable dilator tip and distal loop; and
    an elongate tract comprising a polymer thread adapted and dimensioned to reside within an internal channel of the endoscope, the elongate tract being affixed to the distal loop of the gastrostomy feeding tube and extending proximally through the passageway therefrom;
    wherein the elongate tract extends beyond the proximal end of the gastrostomy feeding tube by a sufficient length and is adapted to be captured and pulled by an ancillary device extending from a distal end of the endoscope through the length of the internal channel, such that the endoscope can advance over the elongate tract to couple with the gastrostomy feeding tube, thereby allowing both to be introduced together through the alimentary tract and into the stomach of a patient.

5. A percutaneous gastrostomy feeding tube system, said system comprising:
    an endoscope;
    a gastrostomy feeding tube having a distal end, a proximal end adapted to engage the endoscope, and
    a coupling member affixed to the gastrostomy feeding tube, the coupling member accessible about the proximal end of the gastrostomy feeding tube and configured to releasably couple to the endoscope or an instrument residing thereinside can releasably couple with the coupling member so that the gastrostomy feeding tube and the endoscope can be introduced together through the alimentary tract and into the stomach of a patient and subsequently disengaged therefrom; wherein the coupling member comprises an elongate tract extending beyond the proximal end of the gastrostomy feeding tube and adapted to extend through a longitudinal channel of the endoscope; and wherein the gastrostomy feeding tube comprises a removable first portion that includes the distal end, and a second portion that includes the proximal end, the first portion being adapted to be removed from the second portion after placement in the patient such that the second portion can remain partially within the patient to maintain external access to the stomach of the patient, and wherein the elongate tract is attached about the first portion.

6. The system of claim 5, wherein the elongate tract comprises a thread or a suture.

7. The system of claim 6, wherein the elongate tract is of a braided configuration.

8. The system of claim 6, wherein the elongate tract comprises a material having high tensile strength such that the elongate tract is resistant to breakage.

9. The system of claim 6, wherein the gastrostomy feeding tube further includes a distal loop with an elongate tract being attached about the proximal end thereof.

10. A percutaneous gastrostomy feeding tube system, said system comprising:

a gastrostomy feeding tube having a passageway extending therethrough, a distal end, a proximal end, a removable first portion and a second portion, the first portion, which includes the distal end, being adapted to be removed from the second portion and being configured and adapted for introducing the second portion within the stomach of a patient, the second portion including a passageway extending therethough and an end cap located about the proximal, the end cap having an inner surface;

an endoscope; and an elongate tract adapted for passage through a channel of the endoscope, the elongate tract having a distal end and a proximal end, the distal end of the elongate tract adapted to be attached about the removable first portion of the gastrostomy feeding tube, the tract extending through the passageway and beyond the end cap, wherein the distance of the tract from the inner surface of the end cap to the proximal end of the tract is configured to exceed the length of the endoscope channel.

11. The system of claim 10, wherein the elongate tract extends at least 130 cm from the distal end of the gastrostomy feeding tube.

12. The system of claim 10, wherein the elongate tract comprises a braided wire.

13. A percutaneous gastrostomy feeding tube system, said system comprising:

a gastrostomy feeding tube having a passageway, a distal end, a proximal end adapted to receive and engage the endoscope, and an end cap located about the proximal end, the distal end including a discardable dilator tip and distal loop;

an endoscope; and an elongate tract comprising a polymer thread adapted and dimensioned to reside within an internal channel of the endoscope, the elongate tract being affixed to the distal loop of the gastrostomy feeding tube and extending proximally through the passageway therefrom;

wherein the elongate tract extends beyond the proximal end of the gastrostomy feeding tube by a sufficient length and is adapted to be captured and pulled by an ancillary device extending from a distal end of the endoscope through the length of the internal channel, such that the endoscope can advance over the elongate tract to couple with the gastrostomy feeding tube, thereby allowing both to be introduced together through the alimentary tract and into the stomach of a patient.

* * * * *

UNITED STATES PATENT AND TRADEMARK OFFICE
CERTIFICATE OF CORRECTION

PATENT NO.   : 6,808,519 B2                                                              Page 1 of 1
DATED        : October 26, 2004
INVENTOR(S)  : Robert D. Fanelli et al.

It is certified that error appears in the above-identified patent and that said Letters Patent is hereby corrected as shown below:

Column 6,
Line 14, after "extending" delete "therethough" and substitute -- therethrough --.

Signed and Sealed this

Twenty-fifth Day of April, 2006

JON W. DUDAS
*Director of the United States Patent and Trademark Office*